United States Patent [19]

Englund et al.

[11] Patent Number: 4,520,652
[45] Date of Patent: Jun. 4, 1985

[54] SYSTEM FOR OBTAINING EXHAUST SAMPLES AND ANALYZING THE SAME

[75] Inventors: Michael S. Englund; Joseph C. Hafele, both of Peoria; Dwain C. Schulze, Jr., North Pekin, all of Ill.

[73] Assignee: Caterpillar Tractor Co., Peoria, Ill.

[21] Appl. No.: 461,727

[22] Filed: Jan. 28, 1983

Related U.S. Application Data

[62] Division of Ser. No. 311,858, Oct. 16, 1981, Pat. No. 4,386,534.

[51] Int. Cl.³ .......................... G01N 1/24; G01N 1/26
[52] U.S. Cl. .......................................... 73/23; 73/863
[58] Field of Search ........... 73/863.12, 863.21, 863.23, 73/23, 863

[56] References Cited

U.S. PATENT DOCUMENTS

| | | | |
|---|---|---|---|
| 3,304,783 | 2/1967 | Quigley | 73/863.12 |
| 3,481,200 | 12/1969 | Ludecke et al. | 73/863.12 |
| 3,593,023 | 7/1971 | Dodson et al. | 73/863.12 |
| 3,603,155 | 9/1971 | Morris et al. | 73/863.12 |
| 3,903,745 | 9/1975 | Bolser | 73/863.21 |
| 3,950,136 | 4/1976 | Bellinga | 73/863.52 |
| 4,079,622 | 3/1978 | Cocola et al. | 73/863.12 |
| 4,090,392 | 5/1978 | Smith et al. | 73/863.33 |

OTHER PUBLICATIONS

Carlson, David H., "The Monitoring of Diesel Pollutants in Underground Mines", Soc. of Mining Engineers of AIME, Reprint No. 79–69, Jan. 1979.

*Primary Examiner*—Stewart J. Levy
*Assistant Examiner*—Hezron E. Williams
*Attorney, Agent, or Firm*—Wood, Dalton, Phillips, Mason & Rowe

[57] ABSTRACT

A system for obtaining samples of the exhaust of a combustor for subsequent constituent level analysis and a method of determining constituent levels. The system includes inlets (10,26) for alternately delivering exhaust or ambient air to the system. System outlets (56,58) are sealingly coupled to sample receiving and collecting containers (60,62) and a pump (32) is connected to the inlets (10,26) to pressurize gases entering the system. The pump has an outlet (32) to an air cooled heat exchanger (38) which is cooled by a fan (40) to condense water vapor in the gases. The heat exchanger is connected by plumbing (48,50,52,64,66) to the system outlets (56,58) and a chemical gas dryer (54) may be connected in the system when ambient air is entering the system inlet (26). The method of analyzing the exhaust includes the steps of partially filling a sample collecting container with dried air and thereafter directing the exhaust to be analyzed into the sample collecting container. The sample is subsequently measured to determine the volumetric levels of at least two constituents and thereafter, the Fuel Specific basis of one of the constituents is calculated utilizing the data obtained in the step of measuring and the normal volumetric level of the other constituent in ambient air.

5 Claims, 2 Drawing Figures

SYSTEM FOR OBTAINING EXHAUST SAMPLES AND ANALYZING THE SAME

This is a division of application Ser. No. 311,858 filed Oct. 16, 1981, now U.S. Pat. No. 4,386,534.

TECHNICAL FIELD

This invention relates to a sampling system for sampling the exhaust stream of a combustor such as an internal combustion engine and a method of utilizing the samples obtained to analyze the exhaust for the level of various constituents.

BACKGROUND ART

Recent years have seen a considerable upsurge in concern for the release of certain undesirable products of combustion into the atmosphere as a result of the operation of internal combustion engines. Among the undesirable products of combustion which are the subject of such concern are oxides of nitrogen as, for example, nitric oxide and nitrogen dioxide, which are referred to generically as "$NO_x$".

While there are many ways to measure and express $NO_x$ emissions from internal combustion engines, the most common are as follows:

1. Volume concentration or PPM, that is, Moles $NO_x \div 10^6$ Moles exhaust;
2. Work Specific or grams $NO_x$ per horsepower hour;
3. Fuel Specific or grams $NO_x$ per gram of fuel burned;
4. Distance Specific or grams $NO_x$ per mile; and
5. Time Specific, grams $NO_x$ per hour.

Typicaly, raw emissions are measured as a volume concentration but to meaningfully assess the impact of $NO_x$ emissions, the same should be related on a specific basis. In particular, to simply know how much $NO_x$ is released does not tell the whole story as such a measurement does not measure the benefits to society as a result of the generation of the $NO_x$ as a by-product of engine usage. It is much more significant to know how much $NO_x$ is released into the atmosphere for a given amount of useful work or a given amount of fuel burned. Thus, Work Specific and Fuel Specific determinations of $NO_x$ emissions provide the most useful and complete information.

Unfortunately, before emissions can be calculated on a specific basis, information in addition to volume concentration, which information is often difficult to measure, must be obtained. To determine a Work Specific emission number, there is required the measurement of exhaust flow and power output. Fuel specific emission determinations require the measurement of exhaust flow and the fuel consumption rate. In laboratories, the obtaining of such numbers is not particularly difficult although sophisticated dynanometer and flow measuring equipment will be required. But the sophistication of equipment required makes in-the-field determinations cumbersome, expensive, and extremely difficult.

In July of 1979, the U.S. Environmental Protection Agency, in the Federal Register of July 23, 1979, proposed a method of determining $NO_x$ emissions on a volume concentration basis corrected to 15% oxygen. In effect, there was proposed a Fuel Specific determination that could be obtained without requiring the measurement of exhaust flow or fuel consumption rate. The technique is based on knowledge of basic combustion, that is, when known quantities of fuel and air are combusted in a lean burning engine, the exhaust product volume concentrations can be easily calculated. A complete derivation of the technique is found in Stationary Internal Combustion Engines—Standard Support and Environmental Impact Statement Volume I; Proposed Standards of Performance EPA—450/2-78-125a July 1979, Appendix C. The technique yields $NO_x$ levels on a Fuel Specific basis corrected to 15% oxygen.

It also illustrates that Fuel Specific $NO_x$ concentrations corrected to 15% oxygen can be obtained by multiplying a measured $NO_x$ volume of concentration obtained in a standard analyzer by 5.9 and dividing the resultant product by 20.9 less the percentage of oxygen measured in the same sample.

However, a certain drawback exists in such a method. At light engine loads, in Diesels, exhaust oxygen concentration may be very nearly equal to 20%. This is quite close to the ambient oxygen concentration of 20.9%. Thus, a small error in the measurement of oxygen in the exhaust can result in a larger percentage error in the calculated $NO_x$ corrected to 15% oxygen.

Some attempts have been made to overcome the foregoing difficulties, particularly in terms of obtaining, in the field, samples suitable for accurate analysis. See, for example, the paper entitled "The Monitoring of Diesel Pollutants in Underground Mines" by David H. Carlson and John H. Johnson, delivered at the annual meeting of the Society of Mining Engineers of AIME in January of 1979. While an improvement, the technique therein described is not altogether satisfactory in that it requires the use of two sampling containers, along with a supply of dry nitrogen and has measurement uncertainties associated with determining dilution ratios of the exhaust gas being measured.

The present invention is directed to overcoming one or more of the above problems.

DISCLOSURE OF THE INVENTION

According to one aspect of the invention, there is provided a system for obtaining samples of the exhaust of a combuster for subsequent constituent level of analysis. The system includes gas inlet means which are alternately adapted to deliver exhaust from the exhaust stream of the combustor or ambient air to the system. A system outlet is provided and is adapted to be sealingly coupled to a sample receiving and collecting container. A pump is connected to the inlet means and is adapted to receive and pressurize gases entering the system through the inlet means and the pump is provided with an outlet for discharge of the gases. An air cooled heat exchanger is connected to the pump outlet to receive gases therefrom and means are provided for flowing air past the heat exchanger to thereby cool the gases therein to condense water vapor in the gases. Means are provided for connecting the heat exchanger to the system outlet to deliver the gases, less the condensed water vapor, from the heat exchanger to the system outlet. There is also provided a chemical gas dryer connectable in the system between the system inlet and the system outlet at least when ambient air is entering the system inlet.

According to another facet of the present invention, there is provided a method of analyzing, on a Fuel Specific basis, the exhaust of a combustor for constituent levels without measuring fuel consumption rates which includes the steps of partially filling a sample collecting container with dried air, thereafter directing the exhaust to be analyzed into the sample collecting container, subsequently measuring the combined dried air and exhaust to determine the volumetric levels of at least two constituents therein each of whose level is changed by combustion from the level present in ambient air, and thereafter calculating the Fuel Specific basis level of one of the constituents utilizing the data obtained in the step of measuring and the normal volumetric level of the other constituent in ambient air.

In a highly preferred embodiment of the method according to the immediately preceding facet of the invention, the other constitutent is carbon dioxide.

Other objects and advantages of the invention will become apparent from the following specification taken in connection with the accompanying drawings.

BEST MODE FOR CARRYING OUT THE INVENTION

Figure 1:
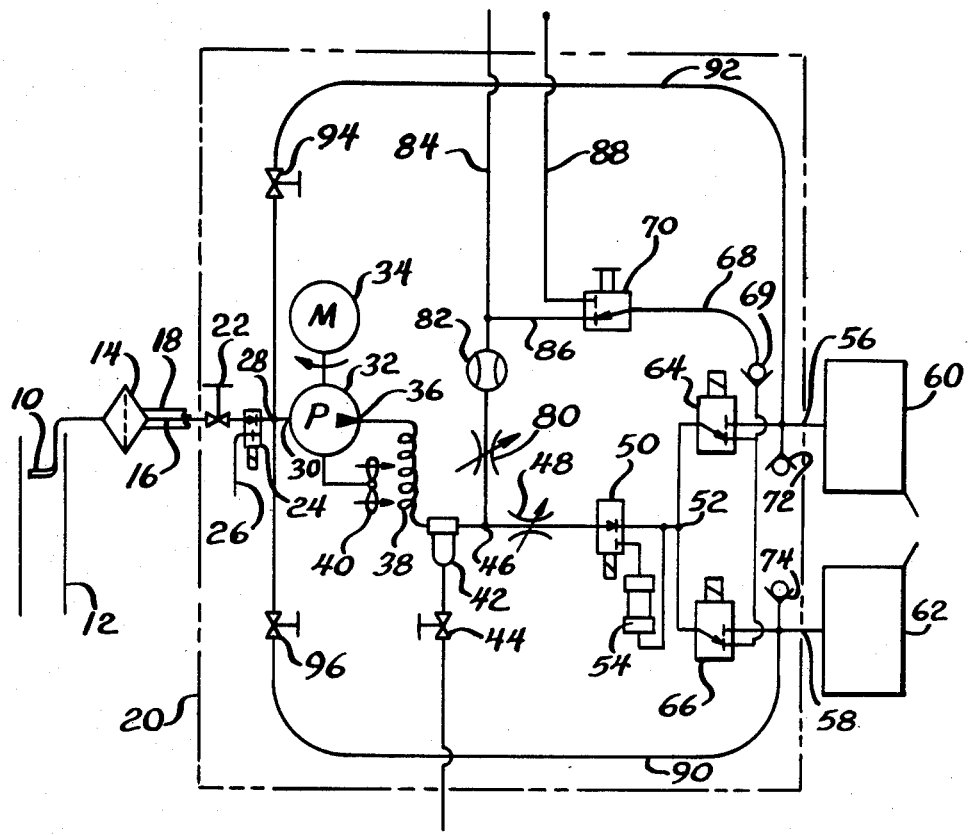
FIG. 1 is a schematic view of one embodiment of a sample obtaining system made according to the invention.

An exemplary embodiment of a system for obtaining samples of the exhaust of a combustor and made according to the invention is illustrated in FIG. 1. The same includes a probe 10 made of stainless steel or other appropriate materials which is adapted to be disposed in the exhaust pipe 12 of the combustor whose exhaust is to be subsequently analyzed. And in the usual case, the combustor will be an internal combustion engine. The probe 10 is connected to a high temperature filter 14 for removing any particulate matter in the exhaust stream being sampled and passing into the system from the probe 10. For example, when sampling the exhaust of a Diesel engine which is likely to have a higher particulate content than a spark ignition engine, the filter 14 is useful in removing such particulates.

Outflow from the filter 14 is via a flexible line 16 which is insulated by any suitable flexible insulation 18.

Line 16 extends to a housing shown schematically at 20 which houses the vast majority of the components of the system. As will be seen, within the housing 20, means are provided for removing water vapor from the exhaust being sampled and the insulation 18 applied to the line 16 prevents the line 16 from becoming sufficiently cool as to allow appreciable condensation to occur prior to the entry of the exhaust into the system components within the housing 20.

Within the housing 20, the line 16 extends to a manually operated valve 22 which will be opened when a sample is to be taken and which may be closed when the system is not in use to prevent the entry of foreign material into the system.

Downstream of the valve 22 is a solenoid operated valve 24. An ambient air inlet 26 within the housing 20 is associated with the valve 24 and the latter is such that when not energized, a junction 28 in the plumbing within the housing is in fluid communication with the valve 22 while when the valve 24 is energized, fluid communication between the junction 28 and the valve 22 is cut off while the junction 28 will be placed in fluid communication with the ambient air inlet 26.

The inlet 30 of a pump 32 is connected to the junction 28. The pump 32 is driven by a motor 34 and pressurizes gases received from either the ambient air inlet 26 or the probe 10.

The pump 32 has an outlet 36 which is connected to a heat exchanger or cooling coil 38. A fan 40, also driven by the motor 34, flows ambient air across the cooling coil 38. This in turn cools the gas flowing through the coil 38 such that a substantial amount of the water vapor in the gas will condense to be received in a water trap 42 connected to the outlet of the cooling coil 38. A valve 44 may be utilized to periodically drain the water trap 42.

The pressurized gas exiting the cooling coil 38 will flow through the water trap 42 to a tee 46 and hence to a valve 48. From the valve 48, the pressurized gas is passed to a solenoid operated valve 50. When the valve 50 is deenergized, the pressurized gas will flow therethrough to a tee 52. Conversely, when the solenoid valve 50 is energized, the pressurized gas will be directed to the junction 52 via a chemical dryer 54 containing any suitable disiccant.

From the tee 52, the pressurized gas is directed to a first or second system outlet 56 or 58, respectively. Each of the outlets 56 and 58 is adapted to have sealingly coupled thereto, a bag 60 and 62, respectively, which serve as sample receiving and collecting containers. While not shown herein, each of the bags 60 and 62 is typically provided with a valve which may be selectively opened or closed to retain a collected sample therein. As is well known, such bags are flexible and plastic and thus, the flow of gas into either from its associated system outlet 56 or 58 causes the same to be inflated.

Control over the flow of gas to one or the other or both of the outlets 56 and 58 is accomplished by first and second solenoid operated valves 64 and 66, respectively. When both of the valves 64 and 66 are energized, pressurized gas will flow from the tee 52 to both of the bags 60 and 62. Conversely, when the valve 64 only is energized, there will be flow only to the bag 60 and flow to the bag 62 will be blocked. When only the valve 66 is energized, there will only be flow to the bag 62. When both of the valves 64 and 66 are deenergized, the flow will be placed upon a line 68 extending to a pressure relief valve 69 and then to a manually operable valve 70.

Pressure regulation within the system is provided and to this end, each of the outlets 56 and 58 has an associated pressure relief valve, 72 and 74, respectively. The valves 72 and 74 may be adjustable if desired but typically will be set to vent the system when the pressure therein exceeds a value on the order of 15 inches of water and the valve 69 set somewhat higher as to open at one PSI.

Returning to the tee 46, another branch extends to a further manually operable needle valve 80 which in turn extends to a flow meter 82 and then to a vent line 84. Through appropriate manipulation of the flow control valves 48 and 80, any suitable flow rate can be obtained. In addition, the valve 80 and the flow meter 82 can be utilized to determine that the pump 32 is operating properly.

Returning to the valve 70, the same is normally in the position illustrated and includes a connection 86 to the vent line 84. Thus, for the configuration of the components illustrated, the pump 32 may be in operation and all gas received and pressurized by it will be vented.

The valve 70 also includes an outlet connected to a line 88 which may be connected directly to a sample analyzer if a sample analyzer is immediately available so that samples may be taken and analyzed without resort to the use of sample collection in the bags 60 and 62. One need merely energize the pump 32 and switch the valve 70 from the position shown to deliver the sampled exhaust directly to the analyzer.

Each of the outlets 56 and 58 have a connection via respective lines 90 and 92 to the junction 28, and thus to the inlet 30 of the pump 32. Each of the lines 90 and 92 is valved as at 94 and 96. When samples are to be taken, the valves 94 and 96 will be closed. However, if it is desired to empty the bags 60 and 62 so that the same may be reused, such may be accomplished by closing the valve 22 while opening the valves 94 and 96, maintaining the valves 64 and 66 in a deenergized state. The samples collected within the bags 60 and 62 will be evacuated and ultimately discharged through the vent 84.

Figure 2:
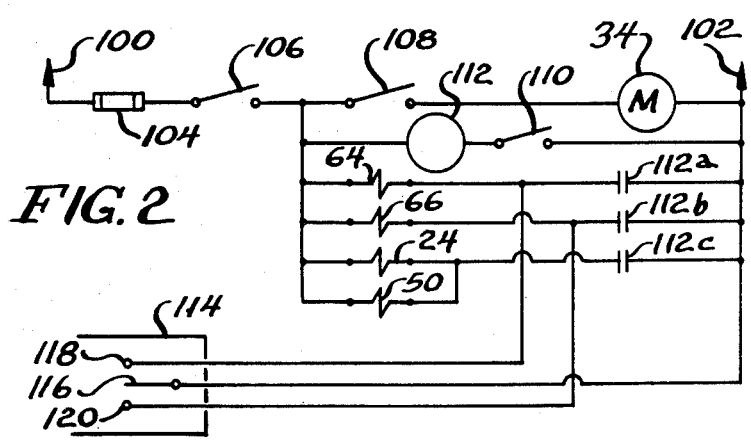
FIG. 2 is an electrical control schematic for certain of the components illustrated in the system in FIG. 1.

An electrical control system is illustrated in FIG. 2 and is seen to include a pair of leads 100 and 102 which may be connected to the usual electrical system of the combustor whose exhaust is to be measured. A fuse 104 is connected in one of the leads as is a main power switch 106. With the switch 106 closed, the system is conditioned for operation. The closing of a further switch 108 will result in energization of the motor 34 to drive the pump 32 and the fan 40. Still another switch 110 is in series with the coil 112 of a relay across the power source when the switch 106 is closed. By closing the switch 110, the relay coil 112 will be energized to cause normally open contacts 112a, 112b, and 112c of the relay to close.

The contacts 112a are in series with the solenoid valve 64 and will accordingly energize the valve 64, when closed. The contacts 112b are in series with the solenoid valve 66 and, when closed, will likewise energize the valve 66. The contacts 112c are in series with the parallel combination of the solenoid valve 24 and the solenoid valve 50 and, when closed, will cause both such valves to shift from the position illustrated in FIG. 1.

The electrical system includes a remote, three position switch 114. The blade 116 of the switch is connected to the lead 102 and is shown in a nonconducting position, one of the three positions provided by the switch 114. In another position of the switch blade 116, the lead 102 will be connected to a contact 118 which is in parallel with the contacts 112a. Thus, when the switch blade 116 is moved to a contact with the contact 118, the solenoid valve 64 will be energized by reason of the bypassing of the contacts 112a.

The third position of the switch blade 116 is in contact with a contact 120 which is in parallel with the contacts 112b. Thus, when the switch blade 116 is on the contact 120, the solenoid valve 66 will be energized by reason of the by-passing of the contacts 112b.

It will be appreciated that all of the components of the system other than the leads 100 and 102 which are necessary for connection to an external power source, the switch 114 which may be operated remotely from the sampling apparatus, the bags 60 and 62 and the probe 10 in associated line 16 are contained within the housing 20 thereby providing a readily portable sampling system that may be used easily in the field. Samples may be obtained by the method to be described and the bags 60 and 62 containing such samples need only be disconnected from the apparatus and taken to a suitable location where an analyzer is available. Thus, a readily portable system is provided by the invention.

The system is operated generally as follows for the purpose of collecting samples in the bags 60 and 62. Initially, the switches 106 and 108 are closed thereby energizing the motor 34 to drive the pump 32 and the fan 40. The operator, with the bags 60 and 62 in place on the outlets 56 and 58, then closes the switch 110, which is a normally open switch, which results in the valves 24, 50, 64 and 66 switching from their positions shown in FIG. 1. Consequently, the pump 32 will draw ambient air into the system from the inlet 26, which ambient air will be passed through the chemical dryer 54 and into both the bags 60 and 62. The switch 110 will be maintained closed until the bags 60 and 62 are filled to some pre-determined degree, usually about half filled. This determination is made visually by the operator of the system although obviously, it could be timer controlled in connection with a particular flow rate adjustment of the valve 48.

In any event, the foregoing results in the partial filling of the bags 60 and 62 with dried ambient air. The drying of the air avoids condensation of water vapor within the bags 60 and 62 for the purpose of eliminating any possibility that constituents of the exhaust stream to be sampled could go into solution into such condensed water vapor and thereby cause erroneous results in the subsequent analysis.

The probe 10 is then inserted in the exhaust stream 12 of the combustor whose exhaust is to be analyzed and assuming the same is operating under the conditions for which the samples are to be taken, the operator will first close the switch 116 via the contact 118 which in turn will cause the valve 64 to shift from the position shown in FIG. 1. All other solenoid valves will be deenergized and as a result, exhaust from the exhaust stream will be input to the system via the line 16 to be pressurized by the pump 32 and directed through the condensation coil 38. In the coil 38, the temperature of the incoming stream will be reduced resulting in the condensation of water vapor which will be trapped in the water trap 42. The dewatered exhaust gas will pass directly to the tee 52, by-passing the chemical dryer 54 and into the bag 60 via the valve 64. When the bag 60 is filled, excess exhaust will be vented by the pressure relief valve 72.

When the operator visually or by predetermined countdown, determines that the bag 60 is full, the switch 116 is returned to its neutral position illustrated in FIG. 2 and the valve 64 will revert to the position illustrated in FIG. 1. Incoming exhaust to the system will be vented from the system via the vent 84 at this time until such time as the motor 34 is deenergized.

In the event a second sample is to be taken, the switch 116 will be closed through the contact 120 causing the valve 66 to shift from the position illustrated in FIG. 1. Operation of the system will be the same except that the bag 62 will be filled rather than the bag 60.

If the analyzer is remotely located, and the system is to be utilized to take further samples, the valves (not shown) on the inlets for the bags 60 and 62 are closed and the same removed from their respective outlets 56 and 58 to be transported to the location of the analyzer. New bags may then be installed to take additional samples.

In the event an analyzer is available for direct connection to the system, such may be made to the line 88 and exhaust samples fed directly to the analyzer by shifting the valve 70 manually.

Evacuation of samples from bags such as bags 60 and 62 may be accomplished by the procedure mentioned previously.

One or more of the bags 60 and 62, with sample therein, is connected to a suitable analyzer of conventional construction in the usual fashion. From each sample, the analyzer will measure on a volumetric basis, usually in parts per million, the levels of at least two constituents. Where concern is for $NO_x$ emissions, $NO_x$ levels will, of course, be measured. Conventionally, oxygen levels will likewise be measured. To determine the $NO_x$ Fuel Specific emissions corrected for 15% oxygen, the following equation is used when $NO_x$ and oxygen levels are determined:

$$NO_{x15} = \frac{\text{(Measured } NO_x \text{ volume concentration) (5.9\%)}}{(20.9\% - O_2 \% \text{ Measured})}$$

However, as alluded to previously, inaccurate results may be obtain when oxygen is utilized in the calculation. At light engine loads, the oxygen in Diesel exhaust will be very nearly 20%. This is sufficiently close to the ambient oxygen concentration of 20.9% such that a small error in the oxygen measurement can result in a large percentage error in the calculation $NO_x$ emission adjusted for 15% oxygen.

According to the invention, it is much preferred to measure carbon dioxide rather than oxygen. The observed $NO_x$ concentrations can be corrected to a 15% oxygen reference with a carbon dioxide measurement according to the following equation:

$$NO_{x15} = \frac{\text{(Measured } NO_x \text{ volume concentration) (4.40\%)}}{(CO_2 \% \text{ Measured} - 0.03\%)}$$

In a Diesel running under lightload conditions, the concentration of carbon dioxide in the exhaust generally is on the order of 1.3%. This is about 43 times greater than the concentration of carbon dioxide in ambient air with the result that errors in measurement of the carbon dioxide have a negligible effect in determining $NO_x$ Fuel Specific levels corrected to 15% oxygen. This, in turn, allows the obtaining of accurate results with conventional, readily commercially available, analyzer systems.

INDUSTRIAL APPLICABILITY

The system of the present invention may be utilized to obtain samples for subsequent analysis virtually anywhere including rugged, in-the-field conditions without requiring the presence of sophisticated equipment such as dynamometers or even analyzers in the immediate vicinity. The samples may be taken and transported to the location of an analyzer. Alternatively, if an analyzer is present, the system may be directly connected to such analyzer.

The system is readily portable and simple in nature. It does not require the use of dried nitrogen which, of course, would require a source of such nitrogen in a heavy bottle or the like. Results using the present system are independent of the relative fill of a given bag of ambient air and exhaust.

Moreover, analysis in the highly preferred form of the invention utilizing a measurement of carbon dioxide as opposed to oxygen provides for accurate measurements for Diesel engines where the same are running under lightload conditions without introducing the possibility of large errors due to minor discrepancies in measurement.

While the invention has been disclosed generally in the context of obtaining data regarding $NO_x$ emissions, it will be appreciated that the same apparatus, measurement and calculations procedures may be utilized to determine other constituents in the exhaust stream of a combustor.

We claim:

1. A method of analyzing, on a fuel specific basis, the exhaust of a combustor for constituent levels without measuring fuel consumption rates, comprising:

partially filling a sample collecting container (60,62) with dried air;

thereafter directing the exhaust to be analyzed into said sample collecting container (60,62);

subsequently measuring the combined dried air and exhaust to determine the volumetric levels of at least two constituents therein each of whose level is changed by combustion from the level present in ambient air; and calculating the fuel specific basis level of one of said constituents utilizing the data obtained in the step of measuring, and the normal volumetric level of the other constituent in ambient air.

2. The method of claim 1 wherein said other constituent is carbon dioxide.

3. The method of claim 1 wherein water vapor in the exhaust is at least partially removed during the step of directing and prior to entry of the exhaust into the sample collecting container (60,62).

4. The method of claim 3 wherein water vapor removal is effected by cooling the exhaust with ambient air to condense water vapor without introducing ambient air into the exhaust.

5. The method of claim 1 wherein the step of partially filling includes the step of passing ambient air through a desiccant.

* * * * *